(12) United States Patent
Andersen et al.

(10) Patent No.: US 10,695,499 B2
(45) Date of Patent: Jun. 30, 2020

(54) METHOD OF MANUFACTURING PREFILLED DRUG DELIVERY DEVICES

(71) Applicant: Novo Nordisk A/S, Bagsvaerd (DK)

(72) Inventors: Carsten Schau Andersen, Valby (DK); Simon Roervig, Copenhagen (DK); Steffen Hansen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 87 days.

(21) Appl. No.: 15/770,990

(22) PCT Filed: Oct. 27, 2016

(86) PCT No.: PCT/EP2016/075932
§ 371 (c)(1),
(2) Date: Apr. 25, 2018

(87) PCT Pub. No.: WO2017/072233
PCT Pub. Date: May 4, 2017

(65) Prior Publication Data
US 2018/0304024 A1  Oct. 25, 2018

(30) Foreign Application Priority Data
Oct. 30, 2015  (EP) .................................... 15192347

(51) Int. Cl.
*A61M 5/315* (2006.01)
*A61M 5/31* (2006.01)
(Continued)

(52) U.S. Cl.
CPC ...... *A61M 5/31513* (2013.01); *A61M 5/3146* (2013.01); *A61M 5/31511* (2013.01);
(Continued)

(58) Field of Classification Search
CPC .......... A61M 5/31513; A61M 5/31501; A61M 5/31583; A61M 2207/00;
(Continued)

(56) References Cited

U.S. PATENT DOCUMENTS 6,221,053 B1    4/2001  Walters et al.
7,291,132 B2 *  11/2007 DeRuntz ........... A61M 5/31551
                                                    604/207
(Continued)

FOREIGN PATENT DOCUMENTS

WO   WO-2009105908 A1 *  9/2009  ........ A61M 5/31501
WO      2014/139918 A1    9/2014
(Continued)

*Primary Examiner* — Jermie E Cozart
(74) *Attorney, Agent, or Firm* — Wesley Nicolas

(57) ABSTRACT

The present invention provides a method of manufacturing a prefilled drug delivery device comprising the steps of arranging a piston rod member (20, 22, 120, 122) and a piston rod guide (40, 140) in a housing (10, 110) such that the piston rod member extends through a guide structure (13, 113) fixed in the housing and is surrounded by and operatively coupled with the piston rod guide, whereby rotation of the piston rod guide in a first direction relative to the housing causes distal movement of the piston rod member relative to the guide structure, and vice versa, and rotation of the piston rod guide in a second direction relative to the housing causes proximal movement of the piston rod member relative to the guide structure, and vice versa, and the piston rod guide is in a first state being capable of bi-directional rotation with respect to the housing, bringing a displaceable wall (62, 162) of a variable volume drug reservoir (60, 160) into abutment with a distal end portion of the piston rod member, moving the variable volume drug reservoir proximally relative to the housing to a completely mounted position, and shifting the piston rod guide irreversibly to a second state in which
(Continued)

rotation of the piston rod guide in the second direction relative to the housing is prevented.

7 Claims, 2 Drawing Sheets

(51) Int. Cl.
*B21D 53/00* (2006.01)
*A61M 5/20* (2006.01)
*A61M 5/24* (2006.01)

(52) U.S. Cl.
CPC ............... *B21D 53/00* (2013.01); *A61M 5/20* (2013.01); *A61M 5/31501* (2013.01); *A61M 5/31515* (2013.01); *A61M 5/31583* (2013.01); *A61M 2005/2411* (2013.01); *A61M 2207/00* (2013.01)

(58) Field of Classification Search
CPC ........ A61M 2005/2411; A61M 5/3146; A61M 5/31511; B21D 53/00
See application file for complete search history.

(56) References Cited

U.S. PATENT DOCUMENTS

| | | |
|---|---|---|
| 8,585,658 B2 | 11/2013 | Forstreuter |
| 9,867,945 B2 | 1/2018 | Nzike et al. |
| 2004/0236285 A1 | 11/2004 | Fisher et al. |
| 2007/0129687 A1* | 6/2007 | Marshall .................. A61M 5/20 604/207 |
| 2008/0234633 A1* | 9/2008 | Nielsen .................... A61M 5/24 604/208 |
| 2011/0046567 A1 | 2/2011 | Radmer et al. |
| 2012/0136315 A1 | 5/2012 | Wieselblad et al. |
| 2012/0283659 A1 | 11/2012 | Kouyoumjian et al. |
| 2012/0283662 A1 | 11/2012 | MacDonald et al. |
| 2014/0358093 A1 | 12/2014 | Soerensen et al. |

FOREIGN PATENT DOCUMENTS

| | | |
|---|---|---|
| WO | 2014/139920 A1 | 9/2014 |
| WO | 2014/161952 A1 | 10/2014 |

* cited by examiner

Distal ← → Proximal

METHOD OF MANUFACTURING PREFILLED DRUG DELIVERY DEVICES

CROSS-REFERENCE TO RELATED APPLICATIONS

This application is a 35 U.S.C. § 371 National Stage application of International Application PCT/EP2016/075932 (published as WO 2017/072233), filed Oct. 27, 2016, which claims priority to European Patent Application 15192347.1, filed Oct. 30, 2015, the contents thereof which are incorporated by reference in their entirety.

FIELD OF THE INVENTION

The present invention relates to drug delivery devices suitable for self-administration by a user. More specifically the present invention relates to methods of manufacturing prefilled drug delivery devices.

BACKGROUND OF THE INVENTION

Today, many devices for self-administration of liquid drugs are based on technologies for percutaneous delivery, e.g. injection devices or infusion pumps, or for pulmonary delivery, e.g. inhalers. In the art of such drug delivery devices there is a marked distinction between a so-called prefilled device and a so-called reusable device. The term "reusable device" designates a drug delivery device which employs a user exchangeable drug container, whereas the term "prefilled device" designates a drug delivery device which carries a non-exchangeable drug container that is pre-mounted by the manufacturer. Hence, where the former is adapted to be used for exhaustion of multiple drug containers, the latter is meant to be discarded after emptying of the pre-mounted drug container.

In large scale manufacturing and assembly of prefilled drug delivery devices, such as prefilled injection pens commonly used in the diabetes care segment for administration of e.g. insulin or glp-1, the tolerance chains are likely to result in relative positions of specific internal components varying slightly from device to device. For example, when a drug containing cartridge comprising a slidable piston is attached to a pen housing the piston may not perfectly align with a piston actuator in the pen housing adapted to thrust the piston forward in the cartridge for expelling of the drug, establishing an undesired clearance between the piston and the piston actuator which needs to be eliminated by the user performing an initial priming action before the first dose administration.

WO 2014/161952 (Novo Nordisk A/S) discloses an example of a prefilled injection pen. If this pen is produced using conventional techniques an initial clearance between the piston rod foot and the piston may potentially exist when the pen is supplied from the manufacturer, and the user is therefore advised to perform initial priming to ensure that this potential clearance is eliminated before the pen is used for administering a dose to the body. Initial priming consists of the user setting a small dose and activating the delivery mechanism to expel the set dose. The piston rod foot will thereby be urged distally a predetermined distance by the piston rod. The predetermined distance traveled by the piston rod foot will be sufficient to eliminate any initial clearance between the piston rod foot and the piston, but will also cause a small amount of drug to be discharged from the cartridge.

So, not only is initial priming of a prefilled drug delivery device an additional activity which is imposed on the user it also inevitably leads to some wastage of drug. It is therefore highly desirable to provide a prefilled drug delivery device in which the piston and the piston actuator are always in physical contact such that initial priming is unnecessary.

In WO 2014/161952 the piston rod is propelled by a rotatable piston rod guide, which is driven by energy released from a torsion spring. This piston rod guide is coupled to the housing by a unidirectional ratchet preventing rotation of the piston rod guide in a direction which would correspond to a proximal movement of the piston rod. The piston rod is thus prevented from proximal movements relative to the piston, which is a prerequisite for eliminating the risk of a subsequently introduced air gap between the piston rod foot and the piston. However, paradoxically, the requirement of preventing proximal piston rod movements reduces the flexibility in the assembly process, rendering a large scale manufacturing of such prefilled drug delivery devices more vulnerable to the tolerance chains. In the absence of individual adjustment the device assembly process is based on predefined positioning of the respective components relative to the housing, entailing an inherent degree of variability in the end products.

SUMMARY OF THE INVENTION

It is an object of the invention to eliminate or reduce at least one drawback of the prior art, or to provide a useful alternative to prior art solutions.

In particular, it is an object of the invention to provide a method of manufacturing prefilled drug delivery devices that do not require initial priming by the user.

It is a further object of the invention to provide such a method which is simple to execute and which can be applied without major alterations to a conventional manufacturing setup.

In the disclosure of the present invention, aspects and embodiments will be described which will address one or more of the above objects and/or which will address objects apparent from the following text.

A method embodying the principles of the present invention comprises the steps of (i) arranging a piston rod member and a piston rod guide in a housing such that a) the piston rod member extends through a guide structure fixed in the housing and is surrounded by and operatively coupled with the piston rod guide, whereby rotation of the piston rod guide in a first direction relative to the housing causes distal movement of the piston rod member relative to the guide structure, and vice versa, and rotation of the piston rod guide in a second direction relative to the housing causes proximal movement of the piston rod member relative to the guide structure, and vice versa, and b) the piston rod guide is in a first state being capable of bi-directional rotation with respect to the housing, (ii) subsequent to (i) bringing a displaceable wall of a variable volume drug reservoir into abutment with a distal end portion of the piston rod member, (iii) subsequent to (ii) moving the variable volume drug reservoir proximally relative to the housing to a completely mounted position, and (iv) subsequent to (iii) bringing (e.g. switching or shifting) the piston rod guide irreversibly to a second state in which rotation of the piston rod guide in the second direction relative to the housing is prevented.

Accordingly, in one aspect of the invention a method as defined in the claims is provided. By this method a prefilled drug delivery device, i.e. a drug delivery device comprising a non-exchangeable drug reservoir, can be produced which does not require a user to perform initial priming before carrying out a dose administration.

The inventive method comprises four simple steps which may all be carried out in an initial assembly phase of the prefilled drug delivery device. In step (i) a piston rod member and a piston rod guide are arranged in a housing or casing of the drug delivery device. The piston rod member may be a unitary piston rod structure or may comprise a piston rod and a piston rod foot (piston washer) in combination, where the piston rod foot abuts a distal end portion of the piston rod. For example, if the prefilled drug delivery device takes the form of a pen injection device the housing may be generally cylindrical (e.g. cylindrical or slightly conical) and the piston rod may be arranged so as to extend along a longitudinal axis of the generally cylindrical housing.

The piston rod guide may be an annular or cylindrical element being mountable over the piston rod member, either by sliding along or spiralling about a longitudinal axis thereof. The piston rod member is arranged such that it extends through a guide structure in the housing and such that a distal end portion of the piston rod member is in an initial assembly position.

The guide structure may either form part of the housing or be a separate member which is translationally and rotationally fixed to the housing.

The piston rod member, the piston rod guide, and the guide structure are configured to cause distal motion of the piston rod member relative to the guide structure in response to the piston rod guide being rotated in a first, e.g. clockwise, direction relative to the housing, and to cause rotation of the piston rod guide in the first direction relative to the housing in response to the piston rod member being moved distally relative to the guide structure. Furthermore, the piston rod member, the piston rod guide, and the guide structure are configured to cause proximal motion of the piston rod member relative to the guide structure in response to the piston rod guide being rotated in a second, e.g. counter-clockwise, direction relative to the housing, and to cause rotation of the piston rod guide in the second direction relative to the housing in response to the piston rod member being moved proximally relative to the guide structure. For example, the piston rod member and the guide structure may be threadedly connected, while the piston rod member and the piston rod guide are rotationally interlocked but capable of relative axial motion. In that case the guide structure may comprise a nut member, or at least a protrusion adapted to serve as a helical track follower. Alternatively, the piston rod member and the piston rod guide may be threadedly connected, while the piston rod member and the guide structure are rotationally interlocked but capable of relative axial motion. In that case the guide structure may comprise a spline.

The piston rod guide is initially arranged in the housing in a first state in which it is capable of bi-directional rotation, i.e. capable of both clockwise and counter-clockwise rotation relative to the housing.

In the subsequent step (ii) a displaceable wall of a variable volume drug reservoir is brought into abutment with the distal end portion of the piston rod member. In case the piston rod member comprises a piston rod and a piston rod foot the distal end portion of the piston rod member is a distal end portion of the piston rod foot.

The variable volume drug reservoir may for example be a drug cartridge comprising a cylindrical body closed at one end by a pierceable self-sealing septum and further housing an axially slidable sealing piston. Step (ii) may thereby comprise bringing a surface portion of the piston into abutment with the distal end portion of the piston rod member, e.g. by inserting at least a portion of the drug cartridge into a distal opening of the housing.

Alternatively, the variable volume drug reservoir may comprise a flexible pouch or bag or may be partly flexible and partly rigid.

In the subsequent step (iii) the variable volume drug reservoir is moved proximally relative to the housing to a completely mounted position, defining a final assembly position of the variable volume drug reservoir. In its final assembly position the variable volume drug reservoir is at least axially fixed with respect to the housing. This may be ensured by irremovably attaching a reservoir retaining structure to the distal opening of the housing. Alternatively, radially inwardly protruding studs may be provided in the housing to prevent distal movement of the variable volume drug reservoir, once brought to the completely mounted position.

During the proximal movement of the variable volume drug reservoir relative to the housing the displaceable wall, being in abutment with the distal end portion of the piston rod member, urges the piston rod member proximally until the movement of the variable volume drug reservoir stops. The distal end portion of the piston rod member is thus moved to a final assembly position relative to the guide structure during the positioning of the variable volume drug reservoir relative to the housing without an air gap being introduced between the displaceable wall and the piston rod member.

Notably, the combination of steps (ii) and (iii) will yield comparable end results over the entire range of thus assembled drug delivery devices, irrespective of any dimensional variations caused by the tolerance chains in the production of the constituent components. To establish an abutment between the displaceable wall of the variable volume drug reservoir and the distal end portion of the piston rod member already in step (ii) presupposes that the initial assembly position of the distal end portion of the piston rod member is a position distally of the final assembly position of the distal end portion of the piston rod member.

In the subsequent step (iv) the piston rod guide is irreversibly brought to a second state in which it is capable of only unidirectional rotation relative to the housing. More specifically, in the second state the piston rod guide is prevented from rotating in the second direction relative to the housing. Due to the aforementioned motional relationship between the piston rod member, the piston rod guide and the guide structure, the piston rod member is thus prevented from proximal movement relative to the guide structure, but still capable of distal movement relative thereto, as required to expel a dose from the variable volume drug reservoir during use of the drug delivery device. Hence, it is not possible to separate the piston rod member from the displaceable wall following the execution of step (iv).

Every prefilled drug delivery device assembled according to the above method will thus be void of an initial air gap between the piston rod member and the displaceable wall of the variable volume drug reservoir, allowing a user to prepare for a dose administration without having to carry out an initial priming action.

Step (iv) may be carried out depending on the particular construction of the device. In some exemplary embodiments of the invention, the housing comprises a first circumferential portion having a smooth interior surface and a second circumferential portion having a serrated interior surface, and the piston rod guide comprises a radially deflectable ratchet arm biased towards the housing. Step (iv) then comprises moving the piston rod guide axially with respect to the housing from the first circumferential portion to the second circumferential portion and preventing subsequent movement of the piston rod guide away from the second circumferential portion. The latter may e.g. be accomplished by leading the piston rod guide past one or more inwardly protruding studs on the internal wall of the housing. When the piston rod guide is positioned at the second circumferential portion the radially deflectable ratchet arm interfaces with the serrated interior surface, thereby allowing rotation of the piston rod guide in the first direction relative to the housing and preventing rotation of the piston rod guide in the second direction relative to the housing.

In other exemplary embodiments of the invention, the housing comprises a circumferential portion having a serrated interior surface, and the piston rod guide comprises a bi-stable ratchet arm movable from a first stable position in which an end portion of the bi-stable ratchet arm is deflected away from the serrated interior surface of the housing to a second stable position in which the end portion of the bi-stable ratchet arm engages the serrated interior surface. Step (iv) then comprises moving the bi-stable ratchet arm from the first stable position to the second stable position. The second stable position ensures that the end portion of the bi-stable ratchet arm maintains contact with the serrated interior surface of the housing during use of the prefilled drug delivery device. Particularly, it allows the end portion of the bi-stable ratchet arm to ride over the serrated interior surface when the piston rod guide rotates in the first direction relative to the housing and to firmly engage with a portion of the serrated interior surface during attempts to rotate the piston rod guide in the second direction relative to the housing.

It is noted that either of the above described unidirectional ratchet interfaces between the housing and the piston rod guide may be realised inversely, i.e. where the piston rod guide comprises a serrated exterior surface, and where the housing comprises an interior ratchet arm. Bringing the piston rod guide irreversibly to the second state may then either comprise moving the piston rod guide axially with respect to the housing from a first housing portion having a smooth interior surface to a second housing portion holding the interior ratchet arm, or maintaining the axial position of the piston rod guide while moving at least a portion of the interior ratchet arm radially inwardly from a first stable position to a second stable position.

Regardless of the particular embodiment of the invention, step (iv) may be executed by distal motion relative to the housing of a guide switching structure, or guide shifting structure, being inserted into, or positioned at least partially in, the housing proximally of the piston rod guide. Thereby, interference with the distally inserted variable volume drug reservoir is avoided.

The guide switching structure may be a separate work piece or a constituent part of the prefilled drug delivery device. In case of the former the separate work piece is merely used to mechanically shift the piston rod guide, or the bi-stable ratchet arm, after which it is removed from the housing. In case of the latter the assembly process may include fewer steps since the required distal motion can be obtained as part of the intended arrangement of the guide switching structure in the housing.

In particular embodiments of the invention the guide switching structure is a drive member forming part of a drug delivery mechanism in the prefilled drug delivery device, and when the piston rod guide is in the second state the drive member is axially movable relative to the housing between a dose setting position and a dose expelling position. In the dose setting position the drive member and the piston rod guide are rotationally decoupled, while in the dose expelling position the drive member and the piston rod guide are rotationally interlocked. Thereby, the drive member is capable of rotating relative to the piston rod guide during e.g. a setting of a dose to be delivered from the variable volume drug reservoir, and of slaving the piston rod guide, and through that the piston rod member, when the drug delivery mechanism is activated to expel the set dose.

The drug delivery mechanism may be manually or automatically actuated. In case of the latter, the prefilled drug delivery device may be of the type comprising a spring member capable of delivering energy for rotation and/or translation of the drive member.

In particular embodiments of the invention, the housing is a unitary structure, e.g. of metal or plastic, which covers at least 80% of the variable volume drug reservoir, when the variable volume drug reservoir is in its final assembly position.

In the present context the term "distal" is used in reference to the end of the prefilled drug delivery device, or of the variable volume drug reservoir, from which the drug is expelled, and the term "proximal" is used in reference to the opposite end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "clockwise" and "counter-clockwise", are used, these refer to the appended figures and not necessarily to an actual situation of use. The shown figures are schematic representations for which reason the configuration of the different structures as well as their relative dimensions are intended to serve illustrative purposes only.

Figure 1A:
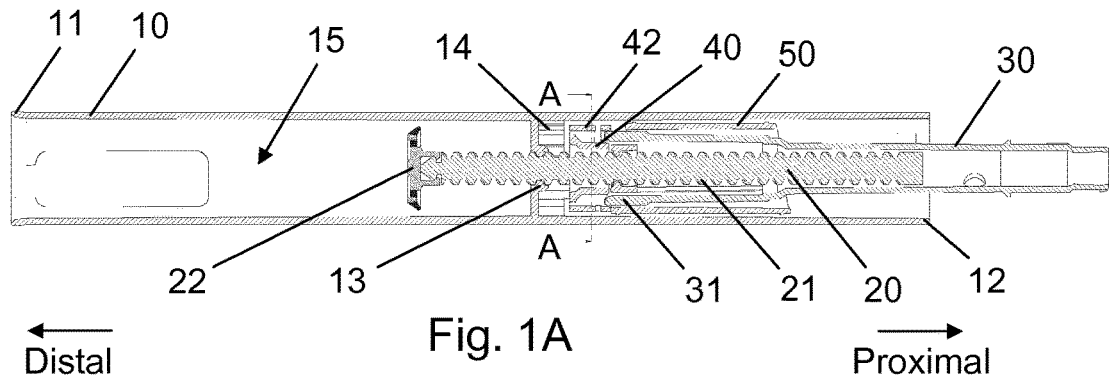
FIG. 1A is a longitudinal section view of an injection device housing carrying components of an actuator mechanism during assembly of a prefilled injection device according to a first embodiment of the invention, notably before insertion of a drug reservoir.
Figure 1B:
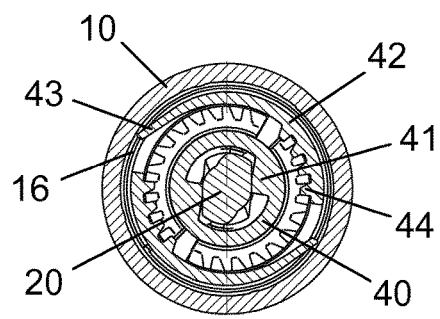
FIG. 1B is a cross-sectional view along line A-A of FIG. 1A.

FIG. 1A is a longitudinal section view of a housing 10 for an injection pen, shown during assembly of the injection pen, and FIG. 1B is a cross-sectional view along line A-A of FIG. 1A. The housing 10 comprises a generally tubular wall extending between an open distal end 11 and an open proximal end 12, and an internal nut member 13 being fixed to an inside portion of the tubular wall in a central region between the distal end 11 and the proximal end 12. A piston rod 20 having a helical thread segment 21 and a non-circular cross-section extends through the nut member 13 and some distance into a chamber 15. The chamber 15 is configured to receive and accommodate a drug reservoir, as will be clear from the below. A piston washer 22 is axially fixed to a distal end portion of the piston rod 20.

Proximally of the nut member 13 a number of constituent components of an actuation mechanism for the injection pen are arranged. Surrounding the piston rod 20 is a rotatable piston rod guide 40 which comprises a peripheral portion 42 and a central portion 41. The peripheral portion 42 carries two diametrically opposite radially deflectable ratchet arms 43 which in an intermediate position of the piston rod guide 40, shown in FIG. 1A, rest on a smooth inner wall surface 16 of the housing 10. The central portion 41 is shaped to mate the non-circular cross-section of the piston rod 20, thereby providing for a rotationally interlocked connection between the piston rod guide 40 and the piston rod 20, and further has teeth 44 along interior surface segments. Just distally of the piston rod guide 40 the housing 10 is provided with a serrated inner wall surface 14 and proximally of the piston rod guide 40 a drive tube 30 and a scale drum 50 are positioned.

The drive tube 30 has a distal toothed rim 31 configured for disengageable mating engagement with the teeth 44 of the central portion 41. The drive tube 30 and the piston rod guide 40 are capable of relative axial motion between a dose setting relative position (shown in FIG. 1A), in which the distal toothed rim 31 is separated from the teeth 44, and a dose expelling relative position, in which the distal toothed rim 31 engage with the teeth 44 and provide a rotationally interlocked relationship between the drive tube 30 and the piston rod guide 40.

Figure 2:
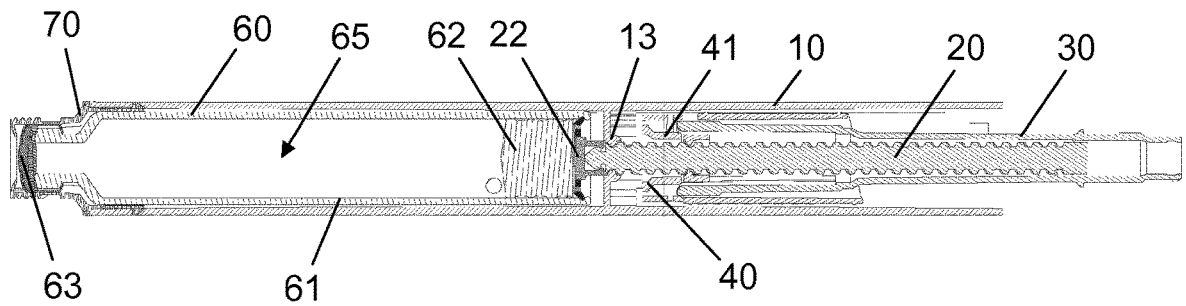
FIG. 2 shows the housing after insertion of a drug reservoir and before final manipulation of a drive component.

FIG. 2 shows the housing 10 with components after insertion of a cartridge 60 through the open distal end 11. The cartridge 60 has a mainly cylindrical side wall 61 which together with a self-sealing penetrable septum 63 at its distal end and a slidable piston 62 opposite the septum 63 define a sealed chamber 65. The chamber 65 holds a drug substance (not visible) and is reducible in volume by distal displacement of the piston 62 following piercing of the septum 63 by a suitable injection needle (not shown).

The insertion of the cartridge 60 is carried out by firstly sliding the side wall 61 axially along the wall of the housing 10 until the piston 62 abuts the piston washer 22, and thereafter pushing the cartridge 60 further into the housing 10, whereby the piston 62 causes a helical displacement, in the proximal direction, of the piston rod 20 relative to the nut member 13, the two being in a non-self-locking thread engagement. The piston rod 20 thereby undergoes a counter-clockwise rotation relative to the housing 10 (seen from the distal end 11) which is made possible by the piston rod guide 40 being in the intermediate position where the ratchet arms 43 can slide unhindered along the smooth inner wall surface 16.

Once the cartridge 60 has been brought to a proximal end of the chamber 15, and thereby is in a completely mounted position, a cartridge holder 70 is non-releasably secured to the distal end 11, effectively fixating the cartridge 60 relative to the housing 10. Notably, the piston washer 22 and the piston 62 are still in abutment in this position of the cartridge 60.

The piston rod guide 40 is now shifted axially until it abuts the proximal face of the nut member 13. This is done by forcing the drive tube 30 distally, whereby the distal end of the toothed rim 31 will abut a radially outwardly protruding section of the central portion 41 and push the piston rod guide 40 along. The piston rod guide 40 thereby simply slides translationally along the piston rod 20, without causing a movement of the latter, surpassing a couple of studs (not visible) on the inside of the housing 10 which prevent the piston rod guide 40 from returning to the intermediate position.

Figure 3A:
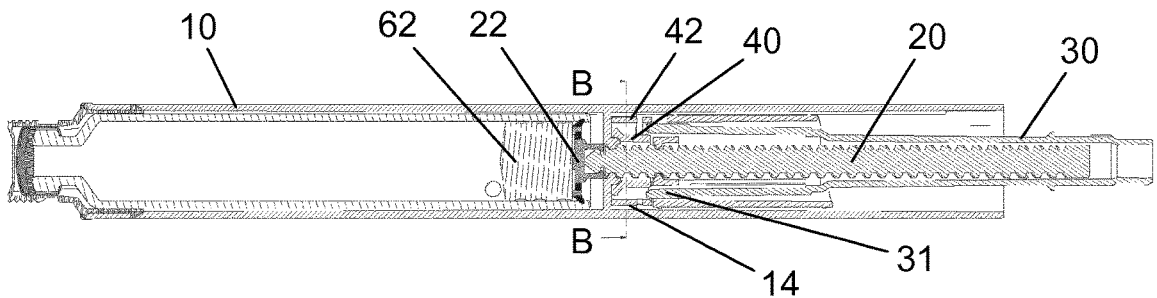
FIG. 3A shows the housing after final manipulation of the drive component.
Figure 3B:
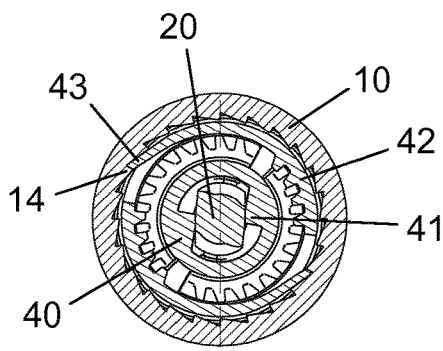
FIG. 3B is a cross-sectional view along line B-B of FIG. 3A.

The position of the piston rod guide 40 next to the nut member 13 is thus the final position of the piston rod guide 40 in the housing. FIG. 3A shows this position after retraction of the drive tube 30. In the final position of the piston rod guide 40 the ratchet arms 43 are aligned with the serrated inner wall surface 14, the alignment providing a ratchet connection which allows only clockwise motion of the piston rod guide 40 relative to the housing 10. The ratchet connection is seen in FIG. 3B, which is a cross-sectional view along line B-B of FIG. 3A.

The piston rod 20 is now prevented from proximal motion relative to the housing 10 because it is unable to rotate counter-clockwise in the nut member 13, and the piston washer 22 thereby stably abuts the piston 62, eliminating the risk of a clearance being established between the two, either later on in the assembly process or during transportation or handling of the final injection pen.

The injection pen may now be finally assembled by the introduction of further components. However, the subsequent assembly steps are outside the scope of the present invention and will therefore not be described in this context.

FIGS. 4-7 show different states of a prefilled injection pen during assembly according to another embodiment of the invention.

Figure 4A:
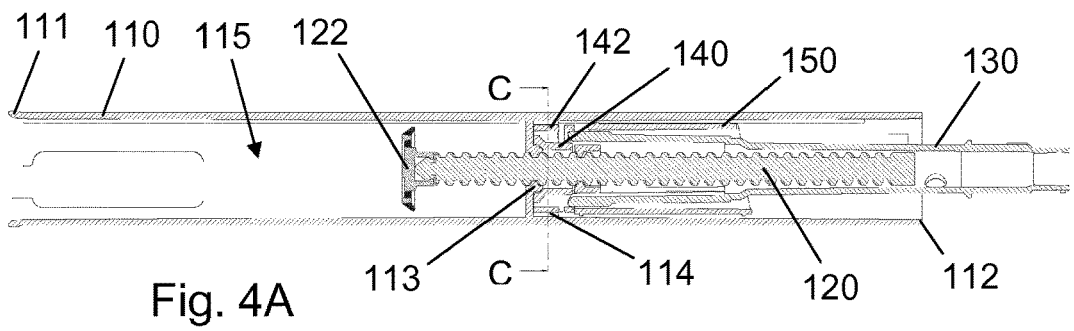
FIG. 4A is a longitudinal section view of an injection device housing carrying components of an actuator mechanism during assembly of a prefilled injection device according to a second embodiment of the invention, notably before insertion of a drug reservoir.
Figure 4B:
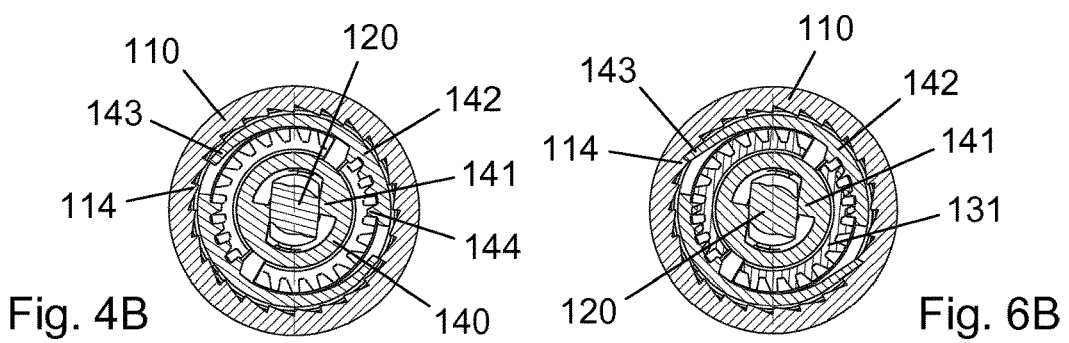
FIG. 4B is a cross-sectional view along line C-C of FIG. 4A.

FIG. 4A is a longitudinal section view of a housing 110 for the injection pen, and FIG. 4B is a cross-sectional view along line C-C of FIG. 4A. The housing 110 comprises a generally tubular wall extending between an open distal end 111 and an open proximal end 112, and an internal nut member 113 being fixed to an inside portion of the tubular wall in a central region between the distal end 111 and the proximal end 112. A piston rod 120 having a helical thread segment 121 and a non-circular cross-section extends through the nut member 113 and some distance into a chamber 115. The chamber 115 is configured to receive and accommodate a drug reservoir, as will be clear from the below. A piston washer 122 is axially fixed to a distal end portion of the piston rod 120.

Proximally of the nut member 113 a number of constituent components of an actuation mechanism for the injection pen are arranged. Surrounding the piston rod 120 is a rotatable piston rod guide 140 which comprises a peripheral portion 142 and a central portion 141. The peripheral portion 142 carries two diametrically opposite bi-stable ratchet arms 143 which in the initial configuration of the piston rod guide 140 shown in FIG. 4B are deflected inwardly and thereby disengaged from a serrated inner wall surface 114 of the housing 110. The central portion 141 is shaped to mate the non-circular cross-section of the piston rod 120, thereby providing for a rotationally interlocked connection between the piston rod guide 140 and the piston rod 120, and further has teeth 144 along interior surface segments. Proximally of the piston rod guide 140 a drive tube 130 and a scale drum 150 are positioned.

The drive tube 130 has a distal toothed rim 131 configured for disengageable mating engagement with the teeth 144 of the central portion 141. The drive tube 130 and the piston rod guide 140 are capable of relative axial motion between a dose setting relative position (shown in FIG. 4A), in which the distal toothed rim 131 is separated from the teeth 144, and a dose expelling relative position (shown in FIG. 6A), in which the distal toothed rim 131 engage with the teeth 144 and provide a rotationally interlocked relationship between the drive tube 130 and the piston rod guide 140.

Figure 5:
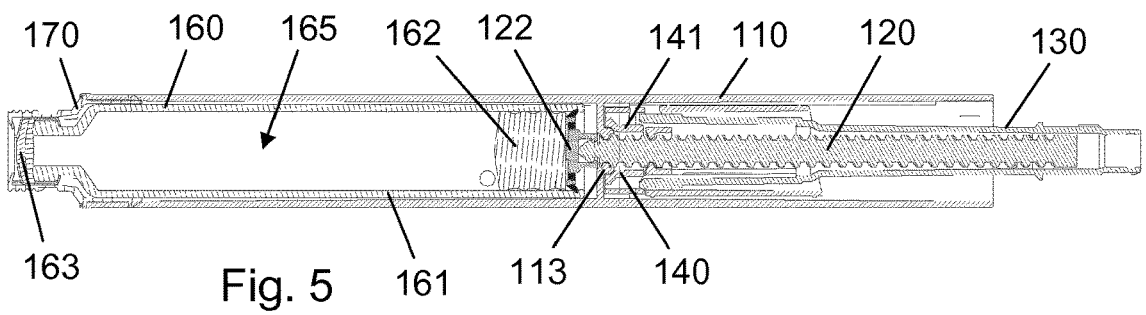
FIG. 5 shows the housing after insertion of a drug reservoir and before final manipulation of a drive component.

FIG. 5 shows the housing 110 with components after insertion of a cartridge 160 through the open distal end 111. The cartridge 160 has a mainly cylindrical side wall 161 which together with a self-sealing penetrable septum 163 at its distal end and a slidable piston 162 opposite the septum 163 define a sealed chamber 165. The chamber 165 holds a drug substance (not visible) and is reducible in volume by distal displacement of the piston 162 following piercing of the septum 163 by a suitable injection needle (not shown).

The insertion of the cartridge 160 is carried out by firstly sliding the side wall 161 axially along the wall of the housing 110 until the piston 162 abuts the piston washer 122, and thereafter pushing the cartridge 160 further into the housing 110, whereby the piston 162 causes a helical displacement, in the proximal direction, of the piston rod 120 relative to the nut member 113, the two being in a non-self-locking thread engagement. The piston rod 120 thereby undergoes a counter-clockwise rotation relative to the housing 110 (seen from the distal end 111) which is made possible by the piston rod guide 140 being in the initial configuration where the bi-stable ratchet arms 143 are disengaged from the serrated inner wall surface 114.

Once the cartridge 160 has been brought to a proximal end of the chamber 115, and thereby is in a completely mounted position, a cartridge holder 170 is non-releasably secured to the distal end 111, effectively fixating the cartridge 160 relative to the housing 110. Notably, the piston washer 122 and the piston 162 are still in abutment in this position of the cartridge 160.

Figure 6A:
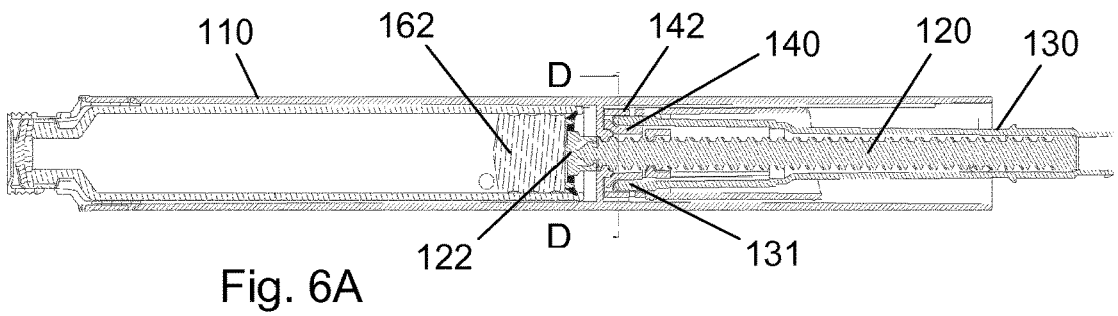
FIG. 6A shows the housing during final manipulation of the drive component.
Figure 7:
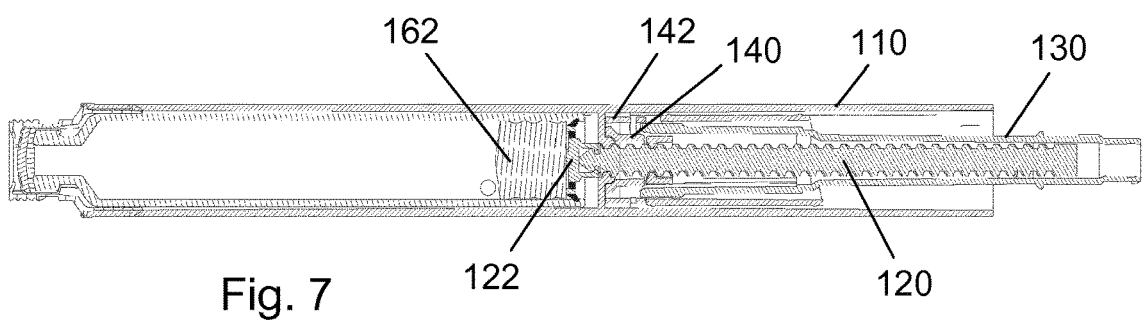
FIG. 7 shows the housing after final manipulation of the drive component.
Figure 6B:
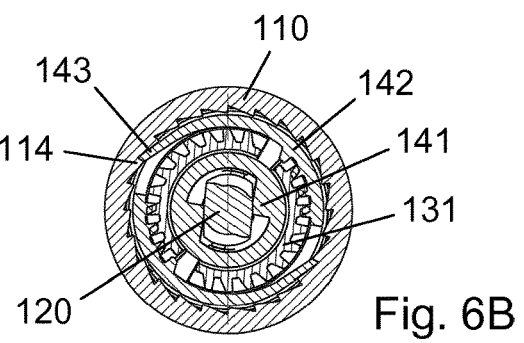
FIG. 6B is a cross-sectional view along line D-D of FIG. 6A.

As seen in FIG. 6A the drive tube 130 is now shifted axially until it abuts a radially outwardly protruding section of the central portion 141. During this movement the toothed rim 131 displaces the bi-stable ratchet arms 143 outwardly and into their other stable position in which they engage the serrated inner wall surface 114, providing a ratchet connection which allows only clockwise motion of the piston rod guide 140 relative to the housing 110. The ratchet connection is seen in FIG. 6B, which is a cross-sectional view along line D-D of FIG. 6A.

With the piston rod guide 140 now being in a final configuration in the housing 110 the piston rod 120 is prevented from proximal motion relative to the housing 110 because it is unable to rotate counter-clockwise in the nut member 113, and the piston washer 122 thereby stably abuts the piston 162, eliminating the risk of a clearance being established between the two, either later on in the assembly process or during transportation or handling of the final injection pen.

Regardless of the specific embodiment of the invention since the final injection pen can be delivered to the user in a state where there is no air gap between the piston and the piston washer the need for an initial priming action is removed and the user may immediately start using the device for dose administration.

The invention claimed is:

1. A method of manufacturing a prefilled drug delivery device of the type comprising a housing extending along a longitudinal axis and having a guide structure fixed therein, a variable volume drug reservoir having a displaceable wall, a piston rod member extending through the guide structure and comprising a distal end portion adapted to interface with the displaceable wall, and a piston rod guide, wherein the piston rod member is operatively coupled with the piston rod guide and configured to undergo axial or helical motion through the guide structure in response to a rotation of the piston rod guide relative to the housing, the method comprising:
   (i) arranging the piston rod member and the piston rod guide in the housing such that
      the piston rod member extends through the guide structure, and the distal end portion is in an initial assembly position, and
      the piston rod guide surrounds a portion of the piston rod member proximally of the guide structure, and is in a first state being capable of bi-directional rotation with respect to the housing, where rotation of the piston rod guide in a first direction relative to the housing causes distal movement of the piston rod member relative to the guide structure, and vice versa, and rotation of the piston rod guide in a second direction relative to the housing causes proximal movement of the piston rod member relative to the guide structure, and vice versa,
   (ii) subsequent to (i) bringing the displaceable wall of the variable volume drug reservoir into abutment with the distal end portion of the piston rod member,
   (iii) subsequent to (ii) moving the variable volume drug reservoir proximally relative to the housing to a completely mounted position, thereby moving the distal end portion to a final assembly position proximally of the initial assembly position, and
   (iv) subsequent to (iii) bringing the piston rod guide irreversibly to a second state in which rotation of the piston rod guide in the second direction relative to the housing is prevented by a unidirectional ratchet mechanism.

2. The method according to claim 1, wherein step (iv) is executed by distal motion of a guide shifting structure being inserted into, or positioned at least partially in, the housing proximally of the piston rod guide.

3. The method according to claim 2, wherein the guide shifting structure is a constituent part of the prefilled drug delivery device.

4. The method according to claim 3, wherein when the piston rod guide is in the second state the guide shifting structure is axially movable relative to the piston rod guide between a dose setting position in which the piston rod guide and the guide shifting structure are rotationally decoupled and a dose expelling position in which the piston rod guide and the guide shifting structure are rotationally interlocked.

5. The method according to claim 1, wherein the housing comprises a first circumferential portion having a smooth interior surface and a second circumferential portion having a serrated interior surface, and the piston rod guide comprises a radially deflectable ratchet arm biased towards the housing, and wherein step (iv) comprises moving the piston rod guide axially with respect to the housing from the first circumferential portion to the second circumferential portion and preventing subsequent movement of the piston rod guide away from the second circumferential portion.

6. The method according to claim 1, wherein the housing comprises a first circumferential portion having a smooth interior surface and a second circumferential portion holding an interior ratchet arm, and the piston rod guide comprises a serrated exterior surface, and wherein step (iv) comprises moving the piston rod guide axially with respect to the housing from the first circumferential portion to the second circumferential portion and preventing subsequent movement of the piston rod guide away from the second circumferential portion.

7. The method according to claim 1, wherein one of the housing and the piston rod guide comprises a circumferential portion having a serrated surface and the other of the housing and the piston rod guide comprises a bi-stable ratchet arm irreversibly movable from a first stable position in which an end portion of the bi-stable ratchet arm is deflected away from the serrated surface to a second stable position in which the end portion of the bi-stable ratchet arm engages the serrated surface, and wherein step (iv) comprises moving the bi-stable ratchet arm from the first stable position to the second stable position.

* * * * *